US006436067B1

(12) United States Patent
Deng et al.

(10) Patent No.: US 6,436,067 B1
(45) Date of Patent: Aug. 20, 2002

(54) POWERED SURGICAL HANDPIECE WITH SUCTION CONDUIT INCLUDING A STEPPED VALVE TO REGULATE FLOW THROUGH THE SUCTION CONDUIT

(75) Inventors: Wenjie Deng, San Jose; Steve Tyler, San Francisco, both of CA (US)

(73) Assignee: Stryker Corporation, Kalamazoo, MI (US)

( * ) Notice: Subject to any disclaimer, the term of this patent is extended or adjusted under 35 U.S.C. 154(b) by 0 days.

(21) Appl. No.: 09/454,113

(22) Filed: Dec. 3, 1999

(51) Int. Cl.$^7$ ................................................ A61M 1/00
(52) U.S. Cl. .................................... 604/32; 606/170
(58) Field of Search .............................. 604/22, 19, 27, 604/35, 30, 50, 118, 119; 606/170, 150, 46, 79, 80, 81, 167, 1

(56) References Cited

U.S. PATENT DOCUMENTS

| 5,492,527 A | 2/1996 | Glowa et al. |
| 6,312,441 B1 | 11/2001 | Deng |

OTHER PUBLICATIONS

Stryker Hummer II Handpiece, assembly drawings, Sep., 1997.

*Primary Examiner*—Brian L. Casler
*Assistant Examiner*—Kevin C. Sirmons
(74) *Attorney, Agent, or Firm*—Flynn, Thiel, Boutell & Tanis, P.C.

(57) ABSTRACT

A surgical handpiece (20) capable of actuating a cutting accessory (24) and drawing a suction through the cutting accessory. The handpiece has a housing (22). A motor (25) internal to the housing drives the cutting accessory. A suction bore (44) extends through the housing. The suction bore is the conduit through which the suction is drawn from the cutting accessory. A valve (52) regulates fluid flow through the cutting accessory and the suction bore. The valve is positionable in a fully opened position, a fully closed position and intermediate positions between the fully opened and closed positions. An indexing assembly (84) mounted to the valve inhibits rotation of the valve when it is placed in at least one intermediate position. This inhibiting of the valve movement provides a tactile indication of the position of the valve when it is located between the fully open and fully closed positions.

29 Claims, 5 Drawing Sheets

POWERED SURGICAL HANDPIECE WITH SUCTION CONDUIT INCLUDING A STEPPED VALVE TO REGULATE FLOW THROUGH THE SUCTION CONDUIT

FIELD OF THE INVENTION

This invention relates generally to powered surgical handpieces that include conduits through which suction is drawn. More particularly, this invention relates to this class of handpiece with a valve that can be set to selectively, accurately, regulate flow through the suction conduit.

BACKGROUND OF THE INVENTION

Endoscopic surgical procedures are routinely performed in order to accomplish various surgical tasks. In an endoscopic surgical procedure, small incisions, called portals, are formed in the patient. An endoscope, which is a device that allows medical personnel to view the surgical site, is inserted in one of the portals. Surgical instruments used to perform a specific surgical task are inserted into other portals. The surgeon views the surgical site through the endoscope to determine how to manipulate the surgical instruments in order to accomplish the surgical procedure. An advantage of performing endoscopic surgery is that, since the portions of the body that are cut open are minimized, the portions of the body that need to heal after surgery are likewise reduced. Moreover, during an endoscopic surgical procedure, only relatively small portions of the patient's internal organs and tissue are exposed to the open environment. This minimal opening of the patient's body lessens the extent to which a patient's organs and tissue are open to infection.

The ability to perform endoscopic surgery has been enhanced by the development of powered surgical tools especially designed to perform endoscopic surgical procedures. One such tool, for example, is sold by the Applicant's Assignee under the trademark HUMMER II. This tool is in the form of a cylindrical handpiece designed to be held in the hand of the surgeon. Internal to the handpiece there is a motor. A front end of the handpiece is provided with a coupling assembly for releasably holding a cutting accessory. The types of cutting accessories that are attached to this handpiece include shavers, resectors, planers and burrs. Integral with the motor and coupling assembly is a means for transmitting the rotary power developed by the motor to the cutting accessory.

The handpiece also has a suction conduit. This is because, in an endoscopic surgical procedure, irrigating fluid is introduced into the surgical site. This fluid serves as a transport media for removing debris from the surgical site. In order to remove the irrigating fluid, and the material in the fluid, a suction path is provided through the cutting accessory and the handpiece. A suction pump is connected to the handpiece and provides the suction force for drawing the fluid and material away from the surgical site. In order to control the suction flow through the cutting accessory and the handpiece, the handpiece is provided with a manually operated valve. Thus, with a single handpiece, a surgeon both manipulates the cutting accessory and controls the suction of material away from the surgical site.

For the above reasons, presently available handpieces have proven to be very useful tools for performing surgical procedures. Nevertheless, there is a limitation associated with the suction systems that are integral with these handpieces. Specifically it is very difficult for a surgeon to regulate the suction rate, the rate at which fluid and debris are drawn away from the surgical site through the handpiece. Presently available handpieces have valves that allow variable control of suction flow through the associated suction conduit. However, it is difficult to precisely set the currently available valves to specific flow rate settings between their fully closed and fully opened positions.

In order to regulate suction through the handpiece conduit, some surgeons rely on an assistant to regulate the operation of the suction pump to which the conduit is attached. In this process, the on-handpiece suction valve is simply placed in the full open state. The surgeon voices commands to the assistant indicating the amount of suction that is desired during various stages of the surgical procedure. Based on these commands, the assistant regulates the setting of the suction pump to regulate the suction drawn from the surgical site. One disadvantage of this system is that the surgeon must verbalize his/her commands. When providing these commands, the surgeon must speak loud enough so that the assistant can hear them over the presence of ambient noise in the operating room. Requiring a surgeon to take this action can detract the surgeon's attention from the surgical site. Moreover, in this control system, in addition to the surgeon speaking the commands, the assistant must hear the commands, mentally process the commands and then manipulate the appropriate control switches to cause the desired changes in suction level. The processing of all these steps means that there can be a significant delay between when the surgeon first decides that the suction flow should be adjusted and the desired adjustment occurs.

One solution that has been suggested to this problem is to provide index marks on the body of the handpiece adjacent the switch member of the valve. The surgeon can then set the valve to a desired position by positioning the switch member relative to the index marks. A disadvantage of this arrangement is that it requires the surgeon to focus his/her eyes on the position of the valve switch member. In order to take this action, the surgeon has to divert his/her eyes and attention from the surgical site. Clearly, it is more desirable for the surgeon's eyes to remain focused on the surgical site and the procedure being performed at the site.

SUMMARY OF THE INVENTION

This invention relates to a new powered surgical handpiece with a suction conduit and a valve that facilitates the accurate control of fluid flow through the suction conduit. The valve of this invention includes an indexing assembly. The indexing assembly provides tactile feedback to the person actuating the valve regarding the position of the valve. Thus, an individual, based on feel alone, can set the valve to at least one known intermediate flow rate state between the full off and full on states.

BRIEF DESCRIPTION OF THE DRAWINGS

The invention is pointed out with particularity in the claims. The above and further advantages of the invention may be better understood by reference to the following description taken in conjunction with the accompanying drawings, in which:

DETAILED DESCRIPTION

Figure 1:
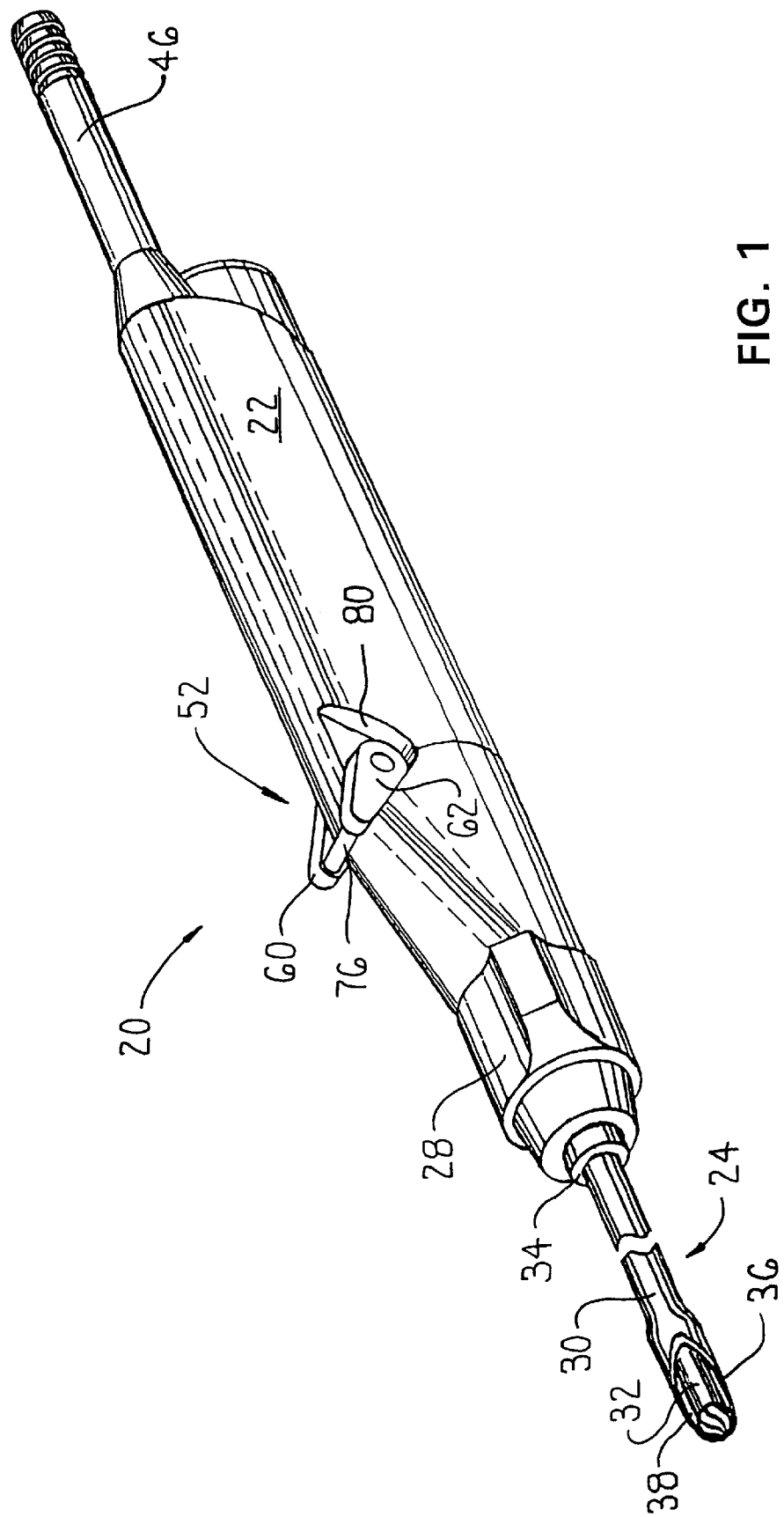
FIG. 1 depicts a powered surgical handpiece of this invention.
Figure 2:
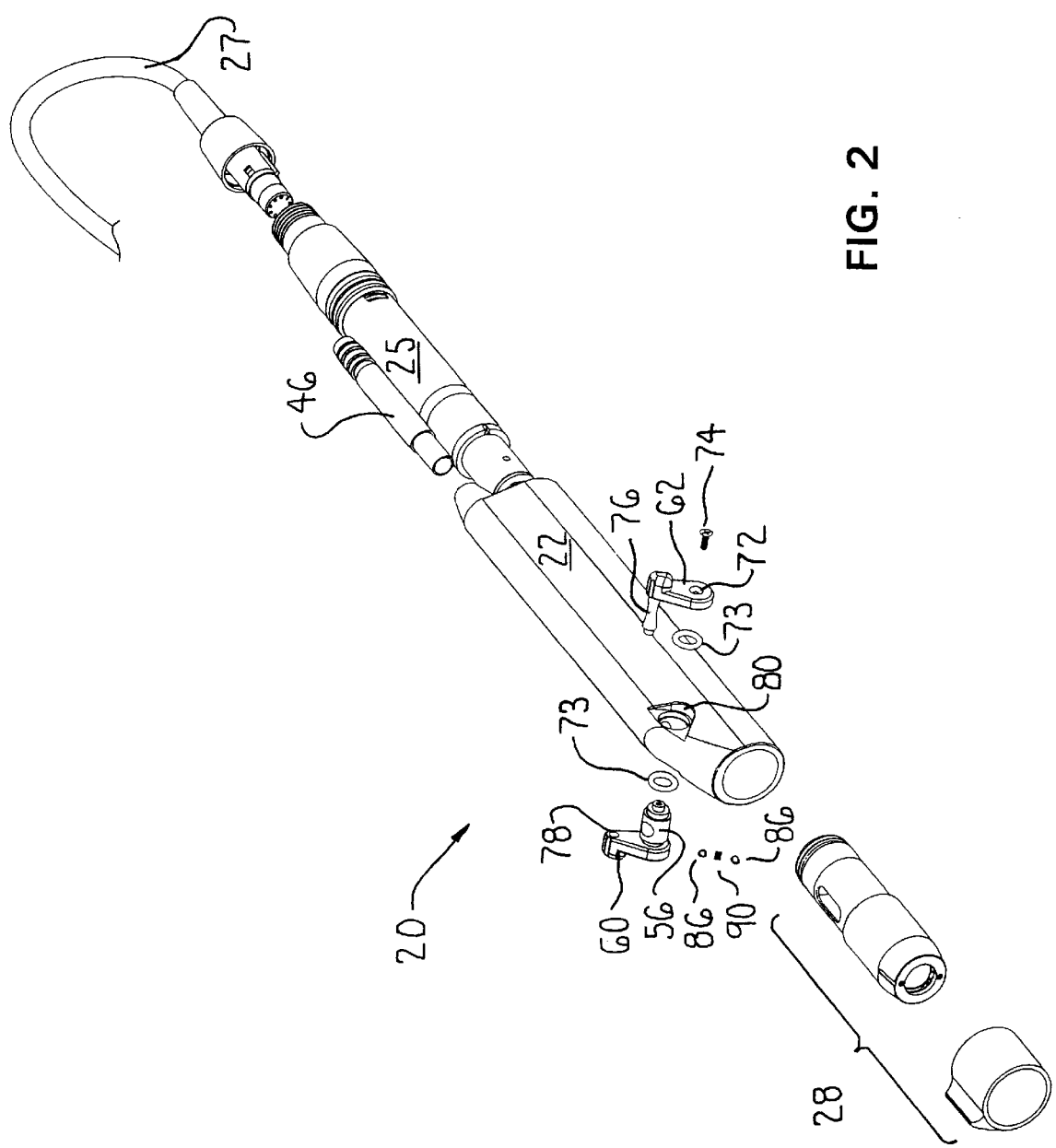
FIG. 2 is an exploded view of the surgical handpiece.

FIGS. 1 and 2 depict a surgical handpiece 20 of this invention. Handpiece 20 is designed to perform endoscopic surgical procedures though not all handpieces of this invention may be so limited. The handpiece 20 includes an elongated housing 22 that forms the body of the handpiece. A complementary cutting accessory 24 is attached to the front end, the distal end, of the handpiece 20. A coupling assembly 28 attached to the distal end of the housing 22 releasably couples the cutting accessory 24 to the handpiece 20. A motor 25 is located inside the housing 22. Power is supplied to motor 25 from a power supply, (not illustrated) through a power cable 27 attached to the proximal rear end of the housing 22.

The cutting accessory 24 includes inner and outer tubes 30 and 32, respectively. A static hub 34 is attached to the proximal, rear end of the outer tube. The static hub 34 is coupled to the coupling assembly 28 to hold the outer tube 30 fixed in place relative to the handpiece housing 22. An inner hub, (not illustrated) is fixed to the proximal end of the inner tube 30 and is seated in the coupling assembly 28. The inner hub engages a drive shaft that extends forward from the motor 25. Thus, the actuation of the motor 25 causes the rotation of the inner tube 30. The distal ends of the inner and outer tubes 30 and 32, respectively, are formed with openings 36 and 38, respectively. Fluid and debris from the surgical site to which the cutting accessory 24 is applied flow through openings 36 and 38 into the center of inner tube 30.

Figure 3:
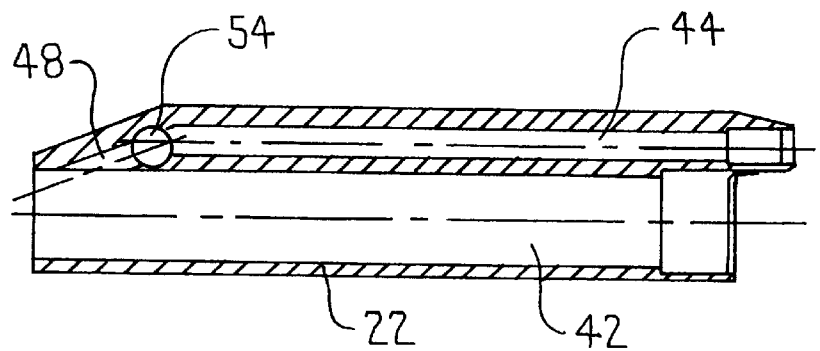
FIG. 3 is a cross sectional view of the handpiece housing depicting the conduit through which a suction is drawn.

As seen best by reference to FIGS. 2 and 3, the handpiece housing 22 is formed to have a large diameter main bore 42. Main bore 42 is the space within housing 22 in which the motor 25 and drive shaft are located. Extending parallel with and located above main bore 42, housing 22 is formed to have a suction bore 44. The suction bore 44 opens at the proximal, rear end of the housing 22. A suction fitting 46 is coupled to the open proximal end, the rear end, of the suction bore 44. A relatively small length suction passage 48 extends diagonally upwardly from the distal end of main bore 42 towards suction bore 44. Suction passage 48 provides fluid communication between the coupling assembly and the cutting accessory inner hub to the suction bore 44. Collectively suction passage 48 and suction bore 44 form the suction conduit through the handpiece 20.

A suction line extends from the open end of the fitting 46 to a suction pump, (line and pump not illustrated). A suction is drawn through the passage 48, the suction bore 44, the fitting 46 and suction line by the pump. This is the suction that draws fluid and debris into cutting attachment openings 36 and 38 and through inner tube 30.

The flow through suction bore 44 is regulated by a valve 52. More particularly, valve 52 is located in a valve chamber 54 formed in the housing 22. In the depicted version of the invention, valve chamber 54 connects suction passage 48 with suction bore 44. Valve 52, seen best in FIGS. 4 and 4A, includes a cylindrical valve barrel 56 that is rotatably seated in the valve chamber 54. The barrel 56 is formed to have a bore 58 that extends perpendicular to and through the longitudinal axis of the barrel. The valve 52 is considered in the fully open state when the longitudinal axis of the barrel bore 58 is aligned with the longitudinal axis of the suction passage 48. When the valve 54 is in this position, there is unrestricted fluid flow from the suction passage 48 through the barrel bore 58 into the suction bore 44. The valve 52 is in the closed state when the barrel 56 is positioned so that the outer wall of the barrel faces the end of the suction passage 48 that opens into the valve chamber 54. When the valve 52 is so positioned, the barrel 56 blocks fluid flow from the suction passage 48 to the suction bore 44.

The valve barrel 56 can be placed in intermediate positions between the fully opened and fully closed states. When the valve barrel 56 is so positioned, fluid flow from the suction barrel 48 downline to the suction bore 44 is partially blocked. This partial blocking of suction flow regulates the amount of suction drawn at the surgical site with the handpiece 20.

The position of the valve barrel 56 is set by displacing lever arms 60 and 62 located adjacent the opposed ends of the valve barrel. A first one of the lever arms, arm 60, is integrally formed with the valve barrel 56. More particularly, it will be observed that opposed bosses 64 and 66 are integrally formed with and extend outwardly from the opposed ends of the valve barrel 56. Lever arm 60 extends perpendicularly away from boss 64 relative to the longitudinal axis that extends through the barrel 56 and the bosses 64 and 66.

The second lever arm, arm 62 is fixedly secured to boss 66. Specifically, a mounting stud 70 extends outwardly from and is formed coaxially with boss 66. Lever arm 62 is formed with a mating bore 72 in which stud 70 seats. A screw 74 that extends through level arm 62 into stud 70 and boss 66 holds the arm to the valve barrel 56.

Lever arm 62, it will be observed, is formed so that a pin 76 extends perpendicularly away from the outer end of the arm. The free end of pin 76 seats in complementary bore 78 formed in the opposed end of lever arm 60. When the valve 52 is mounted to the handpiece housing 22, the bosses 64 and 66 extend through opening in the housing coaxial and contiguous with the valve chamber 54. O-rings 73 that extend around the bosses 64 and 66, provide seals around the opposed ends of the valve barrel 56.

It will be observed that the base ends of the lever arms 60 and 62, the ends adjacent the associated bosses 64 and 66, respectively, have an outer diameter greater than that of the outer diameter of the bosses. These ends of the lever arms 60 and 62 are seated in complementary curved notches 80 formed in the housing 22. Notches 80 are wider than the lever arms 60 and 62. This width of the notches 80 provides the lever arms 60 and 62 room to pivot so that they can be manually positioned in order to set the position of the valve barrel 56.

Figure 4:
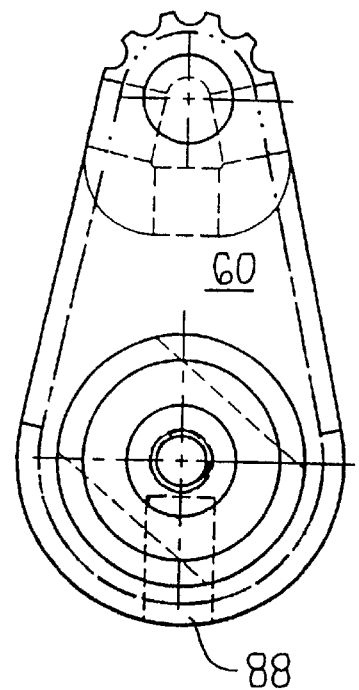
FIG. 4 is side view of the lever arm of the valve integral with the handpiece.
Figure 5:
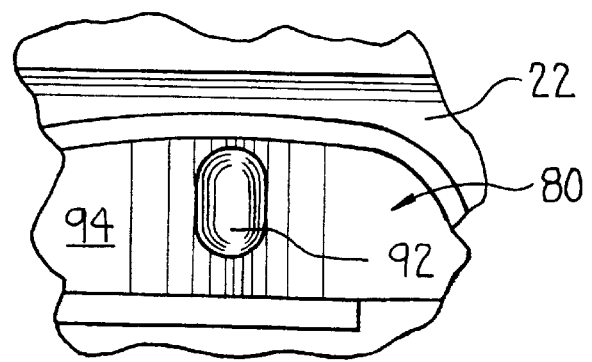
FIG. 5 is a top view of the surface of the handpiece housing over which the lever arm of the valve is seated.
Figure 4A:
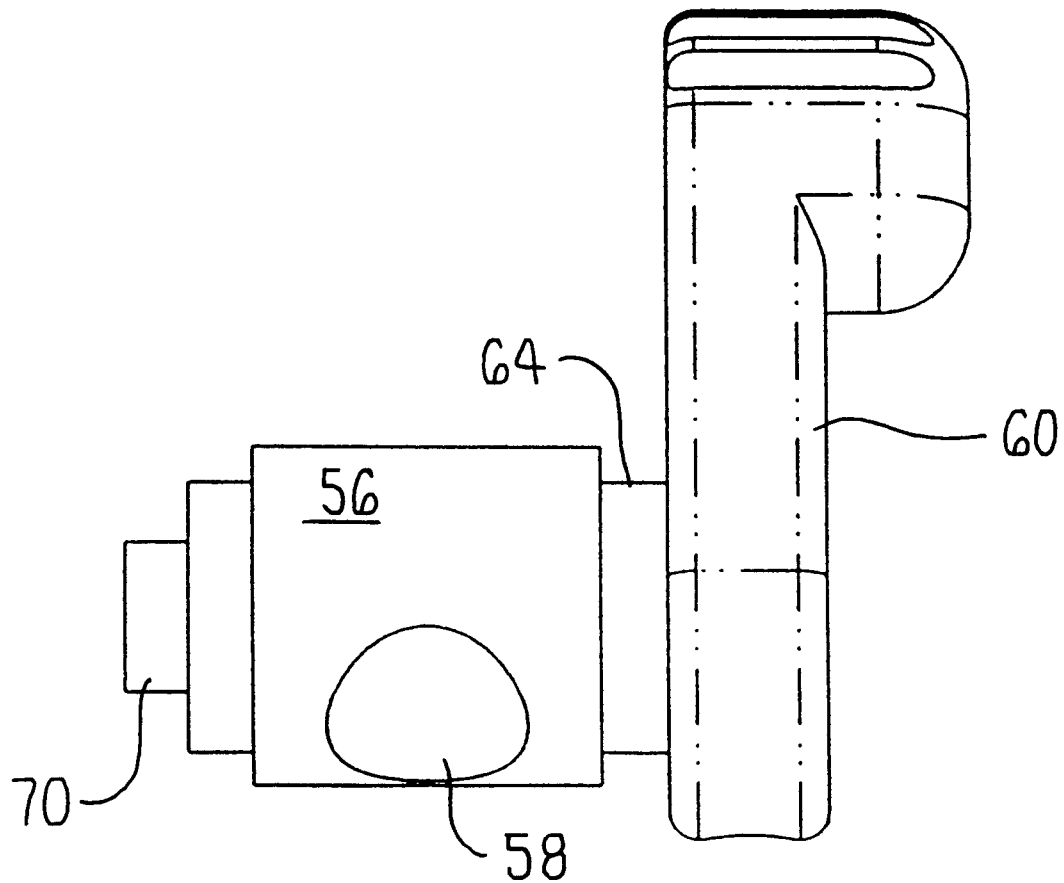
FIG. 4A is a front view of the lever arm depicted in FIG. 4 and the associated valve barrel.
Figure 6:
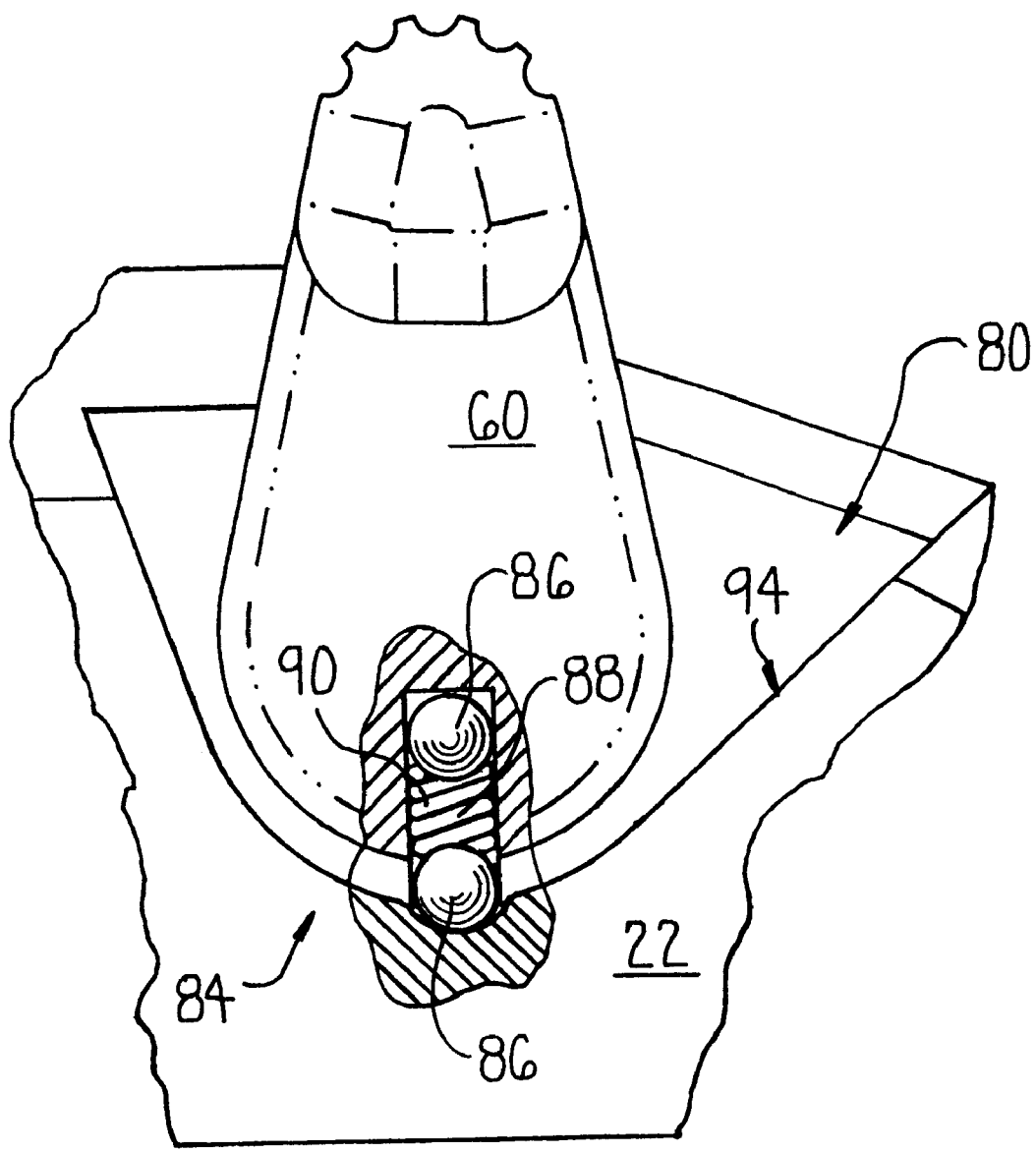
FIG. 6 is a side and exposed view of how the valve indexing assembly of the handpiece of this invention operates.

An indexing assembly 84, now described by reference to FIGS. 4–6, is formed with the housing 22 and valve 52 to provide a tactile indication of when the valve barrel is in intermediate position between the fully open and fully closed states. The illustrated indexing assembly 84 includes a ball 86 formed from a non magnetic sterilizable plastic such as a fluorine resin sold under the trademark Teflon. Ball 86 is partially seated in a bore 88 formed in the base end of lever arm 60 (bore shown in phantom in FIG. 4). Bore 88 extends upwardly from the end of lever arm 60 along the longitudinal axis of the arm. A spring 90 located in the bore 88 pushes ball 86 outwardly. In the depicted version of the invention, a second ball 86 is located in the bore 88 between spring 90 and the base, closed, end of the bore. The second ball 86 is provided for spacing purposes and is not always present.

The indexing assembly 84 also includes an indentation 92 which is formed in the handpiece housing 22. Specifically, indentation 92 is formed in an outer wall 94 of the housing 22 that defines the base of notch 80. Indention 92 is oval shaped and has width equal to or less than the diameter of ball 86.

When the handpiece 20 of this invention is assembled, balls 86 and spring 90 are seated in bore 88 before the valve 52 is fitted to the housing 22. The outermost ball 86 is pushed outwardly by spring 90 and abuts the outer wall 94 of the handpiece housing 22.

The handpiece 22 of this invention is used in the conventional manner. The motor 25 is actuated to cause a like actuation of the inner tube 30. This motion results in the cutting accessory 24 cutting tissue at the surgical site to which the distal end of the accessory is applied.

With the actuation of the suction pump, a suction is drawn from the surgical site through the inner tube 30 and the handpiece housing. The surgeon establishes the level of suction by selectively positioning valve 52. As the level arms 60 and 62 are moved between their full off and full on positions, the ball 86 that extends out of lever arm bore 88 comes into registration with indentation 92. The force of the spring 90 urges the ball 86 into the indentation 92. The seating of the ball 86 in indentation 92 places a small resistance on the further displacement of the valve 52. This resistance momentarily inhibits the otherwise free movement of the valve 52. This inhibiting of the valve movement provides the surgeon with a tactile indication that the valve is in a specific intermediate state between the fully opened and fully closed states.

In one version of the invention, indentation 92 is located so that this intermediate state is the one which corresponds to 50% of the maximum possible flow rate. It should be understood that this position may not be the position that corresponds to the half-way travel position of the valve 52 between the fully open and fully closed states. The exact position of where the valve 56 is located for a given percent of the maximum possible flow rate is identified through either empirical or analytical study.

The surgeon moves the valve 52 out of this intermediate state by the momentary exertion of manual force slightly greater than that which is normally used to position the valve.

The handpiece 20 of this invention is more than a single unit that can be used to simultaneously perform a surgical procedure and draw a suction from a surgical site. The handpiece 20 of this invention has a valve that allows the surgeon to, with the hand used to manipulate the cutting accessory 24, also regulate the suction flow from the surgical site. The valve assembly 52 of this invention gives the surgeon an indication of when it is the fully opened state, the fully closed state and in an intermediate state. The surgeon, based on touch alone, selectively positions the valve 52 to location in which it provides the desired suction. This reduces the extent to which the surgeon has to devote his/her attention to establishing the desired valve setting and/or the extent to which he/she has to provide audible suction commands to an operating room technician that is regulating the suction equipment.

It should be recognized that the forgoing description has been directed to one specific version of the invention. Other versions of the invention may have constructions different from what has been described and illustrated. For example, in not all versions of the invention, will the moving components of the indexing assembly 82 be mounted to the valve 52. In some versions of the invention, the moving components of the indexing assembly 82 are fitted to the handpiece housing 22. In these versions of the invention, a portion of the valve is provided with an indention or recess in which a component mounted to the handpiece housing seats.

Also, there is no requirement that, in all versions of the invention, the described components form the indexing assembly. In other versions of the invention, a spring-loaded pin may function as the member that seats in the complementary recess in order to provide the indication that valve is in the intermediate state. In still other versions of the invention, the indexing assembly may have a single moving component. This component, for example, could be a leaf spring. A section of this leaf spring seats in a complementary recess or indentation formed in the component opposite the component to which the leaf spring is mounted. In still other versions of the invention, a plug of elastomeric material could serve as the biasing member that forces the indexing member into the complementary recess.

Moreover, it should also be understood that this invention is not just limited to valves with indexing assemblies that provide tactile feedback when the valves are in a single intermediate position. Other versions of the invention may be constructed so to provide tactile feedback when the valve to which it is attached is in plural, different intermediate positions. For example, in the described version of the invention, plural, spaced apart indentations 92 may be formed in the handpiece housing 22. As the valve is rotated between the fully opened and closed states, the outer ball 86 seats successively in these indentations. Each time the ball so seats, the indexing assembly 82 provides the surgeon with a tactile feedback that the valve is in a particular intermediate flow rate state.

Therefore, it is the object of the appended claims to cover all such modifications as come within the true spirit and scope of this invention.

What is claimed is:

1. A surgical handpiece for actuation of a cutting accessory, said handpiece including:
    a housing;
    a motor disposed in said housing;
    a coupling assembly mounted to said housing for releasably coupling the cutting accessory to said housing and to said motor;
    a suction conduit extending through said housing from the coupling assembly through which a suction is drawn from the cutting accessory; and
    a valve assembly mounted to said housing, said valve assembly having: a valve member rotatably movable in said housing for regulating fluid flow through said suction conduit, said valve member being selectively moveable between a fully open state, a fully closed state and partially opened states between the fully opened and fully closed states; a arm connected to said valve member for manually positioning said valve member; an indexing member mounted to said valve member or said arm for engaging a portion of said housing when the valve member is in at least one select partially opened state and; a biasing element separate from said indexing member located between said indexing member and said valve member or said arm for urging said indexing member towards a surface of said housing adjacent said indexing member.

2. The surgical handpiece of claim 1, wherein said housing has an outer surface adjacent said valve assembly that is formed with an indentation in which said indexing member seats.

3. The surgical handpiece of claim 1, wherein said indexing member is a ball.

4. The surgical handpiece of claim 3, wherein said housing has an outer surface adjacent said valve assembly that is formed with an indentation in which said ball seats.

5. The surgical handpiece of claim 1, wherein two said arms are attached to said valve member housing.

6. The surgical handpiece of claim 1, wherein said biasing member is a spring.

7. A surgical handpiece for actuation of a cutting accessory, said handpiece including:
   a housing, said housing being formed with a suction bore;
   a motor disposed in said housing;
   a coupling assembly mounted to said housing for releasably coupling the cutting accessory to said housing and to said motor, wherein said housing is formed so that the suction bore extends from said coupling assembly;
   a manually actuated valve mounted to said housing for regulating fluid flow through the suction bore, said valve having a fully opened position, a fully closed position and being positionable in intermediate positions between the fully opened position and the fully closed position, wherein said valve is rotatable in said housing;
   an indexing member located between said valve and said housing wherein, when said valve is in at least one select intermediate position, said indexing member engages said valve and said housing together to inhibit continued rotation of said valve relative to said housing; and
   a biasing member separate from said indexing member positioned against said indexing member for urging said indexing member against one of said housing or said valve, so that said indexing member inhibits the rotation of said valve and wherein said biasing member is selected so that the force imposed by said biasing member is overcome by application of a manual force.

8. The surgical handpiece of claim 7, wherein the one of said housing or said valve against which said indexing member is held is formed with at least one indentation in which said indexing member seats to inhibit rotation of said valve.

9. The surgical handpiece of claim 7, wherein said biasing member is attached to said valve and is positioned to urge said indexing member against said housing.

10. The surgical handpiece of claim 7, wherein said indexing member is a ball.

11. The surgical handpiece of claim 7, wherein said biasing member is a spring.

12. A surgical handpiece for actuation a cutting accessory, said handpiece including:
   a housing, said housing being formed with a suction bore;
   a motor disposed in said housing;
   a coupling assembly mounted to said housing for releasably coupling the cutting accessory to said housing and to said motor, wherein the housing is formed so that the suction bore extends from said coupling assembly;
   a manually actuated valve mounted to said housing for regulating fluid flow through the suction bore, said valve having a fully opened position, a fully closed position and being positionable in intermediate positions between the fully opened position and the fully closed position, wherein said valve is freely rotatable in said housing; and
   an indexing assembly including: an indexing member mounted to said valve to rotate with said valve; a biasing member extending between said valve and said indexing member for urging said indexing member against an adjacent surface of said housing; and at least one recess formed in the adjacent surface of said housing, the recess being positioned so that when the valve is in a select intermediate position, said indexing member is in registration with the recess and seats the recess.

13. The surgical handpiece of claim 12, wherein said valve has a valve barrel that is rotatably disposed in said housing and a manually actuatable valve arm connected to said valve barrel that is located outside of said housing.

14. The surgical handpiece of claim 13, wherein said indexing member and said biasing member are mounted to said valve arm.

15. The surgical handpiece of claim 13, wherein said biasing member is spring.

16. The surgical handpiece of claim 12, wherein said biasing member and said indexing member are mounted in a bore formed in said valve.

17. The surgical handpiece of claim 16, wherein said biasing member is a spring.

18. A surgical handpiece for actuation of a cutting accessory, said handpiece including:
   a housing;
   a motor disposed in said housing;
   a coupling assembly mounted to said housing for releasably coupling the cutting accessory to said housing and to said motor;
   a suction conduit extending through said housing from the coupling assembly through which a suction is drawn from the cutting accessory; and
   a valve assembly mounted to said housing, said valve assembly having: a valve member rotatably mounted in said housing for regulating fluid flow through said suction conduit, said valve member being selectively moveable between a fully open state, a fully closed state and partially opened states between the fully opened and fully closed states; a arm connected to said valve member for manually positioning said valve member; and an indexing member mounted in said arm and positioned to engage a portion of said housing when said valve member is in at least one select partially opened state said indexing being a ball.

19. The surgical handpiece of claim 18, wherein said housing has an outer surface adjacent said valve assembly that is formed with an indentation in which said ball seats.

20. The surgical handpiece of claim 18, further including a biasing element located between said valve assembly arm and said ball.

21. The surgical handpiece of claim 18, further including a spring located between said valve assembly arm and said ball.

22. A surgical handpiece for actuating a cutting accessory, said handpiece including:
   a housing, said housing being formed with a suction bore;
   a motor disposed in said housing;
   a coupling assembly mounted to said housing for releasably coupling the cutting accessory to said housing and to said motor, wherein said housing is formed so that the suction bore extends from said coupling assembly;

a manually actuated valve mounted to said housing for regulating fluid flow through the suction bore, said valve having a fully opened position, a fully closed position and being positionable in intermediate positions between the fully opened position and the fully closed position, wherein said valve is rotatable in said housing; and an indexing member located between said valve and said housing wherein, when said valve is in at least one select intermediate position, said indexing member engages said valve with said housing to inhibit continued rotation of said valve relative to said housing;

wherein, one of said housing or said valve is formed with at least one indentation in which said indexing member seats to result in the engagement of said valve with said housing.

23. The surgical handpiece of claim 22, further including a biasing member mounted to said valve or said housing that is separate from said indexing member, said biasing member being positioned to urge said indexing member against the other of said housing or said valve.

24. The surgical handpiece of claim 23, wherein said biasing member is a spring.

25. The surgical handpiece of claim 22, wherein said indexing member is a ball bearing.

26. The surgical handpiece of claim 22, wherein: said indexing member is mounted to said valve to rotate with said valve; and said indentation is formed in said housing.

27. A surgical handpiece for actuating a cutting accessory, said handpiece including:

a housing, said housing being formed with a suction bore;

a motor disposed in said housing;

a coupling assembly mounted to said housing for releasably coupling the cutting accessory to said housing and to said motor, wherein said housing is formed so that the suction bore extends from said coupling assembly;

a manually actuated valve mounted to said housing for regulating fluid flow through the suction bore, said valve having a fully opened position, a fully closed position and being positionable in intermediate positions between the fully opened position and the fully closed position, wherein said valve is rotatable in said housing; and an indexing member mounted to said valve to rotate with said valve, said indexing member being positioned to be directed towards said housing;

a biasing member separate from said indexing member that extends between said valve and said indexing member, said biasing member being mounted to said valve to rotate with said valve; and wherein, said housing is formed with an outer surface that defines an indentation that is positioned so that when said valve is in at least one select intermediate position, said indexing member seats in the indentation so as to cause said valve engage with said housing to inhibit continued rotation of said valve relative to said housing.

28. The surgical handpiece of claim 27, wherein said indexing member is a ball bearing.

29. The surgical handpiece of claim 27, wherein said biasing member is a spring.

* * * * *

UNITED STATES PATENT AND TRADEMARK OFFICE
CERTIFICATE OF CORRECTION

PATENT NO. : 6,436,067 B1 Page 1 of 1
DATED : August 20, 2002
INVENTOR(S) : Wenjie Deng It is certified that error appears in the above-identified patent and that said Letters Patent is hereby corrected as shown below:

Column 7,
Line 11, change "valve member bousing" to -- valve member --

Column 8,
Line 50, change "state said indexing being a ball" to -- state, said indexing member being a ball --

Signed and Sealed this

Twenty-fifth Day of February, 2003

JAMES E. ROGAN
*Director of the United States Patent and Trademark Office*